United States Patent [19]

Mathew et al.

[11] Patent Number: 4,868,334

[45] Date of Patent: Sep. 19, 1989

[54] PROCESS FOR THE PRODUCTION OF ANHYDROUS OXIME FROM AN AQUEOUS SOLUTION

[75] Inventors: Chempolil T. Mathew, Randolph; Stephen E. Belsky, Newfoundland; Earl E. McKnight, Mine Hill, all of N.J.

[73] Assignee: Allied-Signal Inc., Morris Township, Morris County, N.J.

[21] Appl. No.: 217,265

[22] Filed: Jul. 11, 1988

[51] Int. Cl.$^4$ .................................. C07C 131/00
[52] U.S. Cl. .................................. 564/264; 203/14
[58] Field of Search ..................... 564/264; 203/14

[56] References Cited

U.S. PATENT DOCUMENTS

| | | | |
|---|---|---|---|
| 2,816,063 | 12/1957 | Christian | 564/264 |
| 3,002,996 | 10/1961 | Meier et al. | 564/264 |
| 3,335,183 | 8/1967 | De Rooij | 564/264 |
| 4,323,706 | 4/1982 | Bonfield et al. | 564/253 |
| 4,349,520 | 9/1982 | Bonfield et al. | 423/387 |
| 4,551,323 | 11/1985 | Mathew et al. | 423/387 |

*Primary Examiner*—James H. Reamer
*Attorney, Agent, or Firm*—Melanie L. Brown; Jay P. Friedenson

[57] ABSTRACT

The present invention provides a simple process for the production of anhydrous oxime by the separation of the oxime from an aqueous solution. The process is advantageous because the potential explosive hazards of current processes are eliminated and the oxime is easily separated from the aqueous phase. The process comprises the steps of:

(a) vaporizing an aqueous oxime solution;
(b) vaporizing a water-immiscible organic solvent for the oxime wherein the boiling point of the solvent is lower than the boiling point of the oxime;
(c) combining the vapors together;
(d) condensing the collected vapors;
(e) removing the organic phase of the condensate from the aqueous phase; and
(f) recovering anhydrous oxime from the removed organic phase.

The anhydrous oxime produced by the present process if useful in applications such as isocyanate condensation and carbamate formation.

21 Claims, 1 Drawing Sheet

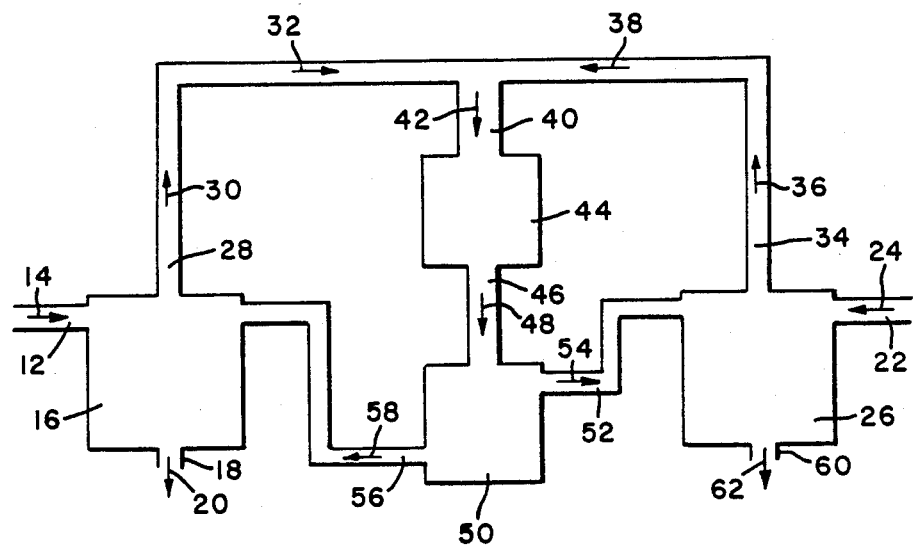

PROCESS FOR THE PRODUCTION OF ANHYDROUS OXIME FROM AN AQUEOUS SOLUTION

BACKGROUND OF THE INVENTION

The present invention relates to a process for the production of anhydrous oxime by separation of the oxime from an aqueous solution.

Oximes may be produced by reacting hydroxylamine with: hexachlorocyclopentadiene as taught by U.S. Pat. No. 3,141,043; cyclic halogenated olefins as taught by U.S. Pat. No. 3,459,802; imino-amines as taught by U.S. Pat. No. 3,462,488; or nitriles as taught by U.S. Pat. No. 4,256,899. Oximes are most generally produced by reacting an organic carbonyl compound such as an aldehyde or ketone with hydroxylamine generated from a hydroxylamine salt such as hydroxylamine sulfate or hydroxylamine chloride. The more economical processes use hydroxylamine sulfate or chloride as aqueous solutions as taught by commonly assigned U.S. Pat. Nos. 3,873,624; 3,931,331; 4,237,069; and 4,323,706; as such, the produced oximes need to be separated from the aqueous system and dried. The need to dry the oxime is more imperative in situations where the oxime is to be used in applications which require anhydrous conditions such as isocyanate condensation and carbamate formation.

Generally, oximes are not very thermally stable and the stability is adversely affected by the presence of acids and bases as well as salts. Two standard processes for the production of anhydrous oxime include: liquid-liquid separation of the water-immiscible oxime from the aqueous oximation mass followed by distillation of the removed oxime phase under reduced pressure to recover the oxime; and liquid-liquid extraction of the aqueous oximation mass with a suitable water-immiscible organic solvent followed by distillation of the organic extract to separate the solvent and recover the oxime as mentioned in U.S. Pat. No. 3,141,043. Such distillation operations encounter build-up of inorganic salt which is carried forward sa salt solution with the oxime to the distillation pot. Heating oxime by itself in the presence of salt can cause the oxime to decompose, and in some instances, decompose so violently so as to explode. As such, the two aforementioned processes for the production of anhydrous oxime are disadvantageous.

If the oxime is partially miscible in water, a standard process for the production of anhydrous oxime involves at least two distillations. In the first distillation, an oxime-water mixture vapor boils over and upon condensation, a two-phase condensate forms; in the second distillation, the water is boiled off and the oxime is recovered. This process is disadvantageous because two distillations are required.

For low boiling oximes such as acetone oxime and acetaldoxime which are freely soluble in water, the task of producing anhydrous oximes by separating the oxime from the aqueous phase is even more difficult because such oximes distill over as water-miscible azeotropes.

Because the aforementioned hazards and difficulties exist in standard processes for the production of anhydrous oxime by separation of oxime from an aqueous phase, a need exists for a simple process for the production of anhydrous oxime by separation of oxime from an aqueous phase wherein the foregoing hazards and difficulties are eliminated.

SUMMARY OF THE INVENTION

The present invention provides a simple process for the production of anhydrous oxime by separation of the oxime from an aqueous phase. The process comprises the steps of:

(a) vaporizing an aqueous oxime solution;

(b) vaporizing a water-immiscible organic solvent for the oxime wherein the boiling point of the solvent is less than the boiling point of the oxime;

(c) combining the vapors together;

(d) condensing the collected vapors;

(e) removing the organic phase of the condensate from the aqueous phase; and (f) recovering anhydrous oxime from the removed organic phase.

If the aqueous oxime solution is prepared by using a salt such as by the treatment of an aldehyde or ketone with hydroxylamine salt and an inorganic base, the aqueous oxime solution contains salt. When using another preparation method, the aqueous oxime solution might not contain salt. During the vaporization of the aqueous oxime solution in step (a) above of the present process, the aqueous oxime solution forms an oxime-water azeotrope vapor while any inorganic salt present in the aqueous oxime solution does not vaporize. As such, any inorganic salt collects as solution on the bottom of the aqueous vaporization pot and is easily removed from the pot. Because the oxime alone is not heated in the presence of salt, the present process eliminates the potential hazards inherent in current processes due to oxime decomposition in the presence of inorganic salt in the distillation pot.

Upon vaporizing the aqueous oxime solution in step (a) above, vaporizing a water-immiscible organic solvent in step (b) above, and combining the vapors together in step (c) above, the water-immiscible organic solvent extracts the oxime from the aqueous oxime solution vapor. Upon condensing the collected vapors together in step (d) above, a two-phase condensate forms wherein the oxime is distributed between the separate organic and aqueous phases. Upon removing the organic phase of the condensate from the aqueous phase in step (e) above, most of the oxime is removed with the organic phase. By selecting an organic solvent having a boiling point which is less than the oxime's boiling point, anhydrous oxime is easily separated from the removed organic solvent by vaporization of the organic solvent.

After removing the organic phase of the condensate from the aqueous phase in step (e) above, the organic phase may be used again in step (b) above. Likewise after removing the aqueous phase of the condensate from the organic phase, the aqueous phase may be used again in step (a) above. As a result of such phase recycling, the present process is more efficient and economical.

As such, the present invention provides a simple and efficient process for the production of anhydrous oxime by separation of oxime from an aqueous phase wherein the potential hazard due to oxime decomposition in the presence of inorganic salt build-up is eliminated and also the oxime is easily separated from the water.

Other advantages of the present invention will become apparent from the following description, attached drawing, and appended claims.

BRIEF DESCRIPTION OF THE DRAWING

THE FIGURE is a schematic illustration of one means for practicing the process of the present invention.

DETAILED DESCRIPTION OF THE PREFERRED EMBODIMENT

The present process is useful for the production of anhydrous oxime by the separation of oxime from an aqueous phase. Any oxime which readily azeotropes with water may be used in the present process. Because simple low molecular weight oximes have such low boiling points and are so freely soluble in water, the present process is particularly useful for the separation of the anhydrous form of these low boiling oximes from an aqueous phase as will be more fully discussed later. The term "low boiling" as used herein refers to oximes having boiling points of less than about 155° C. and preferably, less than about 135° C.

Illustrative examples of low boiling oximes include acetaldehyde oxime or acetaldoxime (bp=115° C.), acetone oxime or acetoxime (bp=135° C.), propionaldehyde oxime or propionaldoxime (bp=132° C.), methylethyl ketoxime (bp=152° C.), n-butyraldehyde oxime or n-butyraldoxime (bp=152° C.), and isobutyraldehyde oxime (bp=152° C.). The preferred oximes for use according to the present invention include acetaldoxime and acetone oxime. These materials are available in commercial quantities or may be prepared by the treatment of the aldehyde or ketone with hydroxylamine salt such as hydroxylamine sulfate or hydroxylamine chloride and an inorganic base such as sodium hydroxide, potassium hydroxide, or ammonia at essentially neutral conditions. An economical source of hydroxylamine salt is Raschig solution which is a dilute aqueous hydroxylamine sulfate solution containing ammonium sulfate and sulfuric acid; Raschig solution is available in commercial quantities.

The concentration of oxime in the starting solution may vary as desired for the present process. It is only necessary that sufficient water is present so that an oxime-water azeotrope forms. Preferably, the starting oxime concentration is about 1 to about 70% by weight, and more preferably, about 5 to about 55% by weight.

The FIGURE illustrates one possible equipment setup for the practice of the present process. It should be understood that the FIGURE is for illustrative purposes only and is not drawn to scale.

After preparation of the aqueous oxime solution which may contain the salt of a base depending upon the preparation method, the aqueous oxime solution is vaporized by any known manner; for example, the aqueous oxime solution may be fed through tube 12 in the direction of arrow 14 into an aqueous stripper or vaporization pot 16. For a continuous mode of operation, the aqueous oxime solution is fed continuously during the process into vaporization pot 16; for a batch mode of operation, the total aqueous oxime solution is placed in vaporization pot 16 at the start of the operation. A conventionally used vaporization pot may be used in practicing this step of the process of the present invention. The aqueous oxime solution is then vaporized to form an oxime-water azeotrope. Although dependent upon the oxime used, the than about 100° C. For an aqueous acetone oxime solution for example, the acetone oximewater azeotrope boils at a temperature of about 97.5° to 98.5° C. For an aqueous acetaldoxime solution for example, the acetaldoxime-water azeotrope boils at a temperature of about 95° to 96° C.

Because the aqueous oxime solution is vaporized, the oxime is stripped of any higher-boiling impurities in the vaporization pot 16. As a result, the product oxime is very pure even though the oxime is not a standard overhead product, i.e., distilled over product.

During the vaporization of the aqueous oxime solution which may contain the salt of a base depending upon the preparation method, the inorganic salt does not vaporize but instead collects on the bottom of the vaporization pot 16. The composition of the inorganic salt depends upon the base which is used in the preparation of the aqueous oxime solution; for example, if sodium hydroxide was used with hydroxylamine sulfate in the preparation of the aqueous oxime solution, sodium sulfate solution collects upon the vaporization of the aqueous oxime solution.

Any any point in the operation of the present process, the residual inorganic salt solution may be removed from the bottom of vaporization pot 16 through opening 18 in the direction of arrow 20 and proper disposal of the salt solution arranged. As mentioned earlier, because the oxime alone is not subjected to heating in the presence of inorganic salt, the present process eliminates the potential for oxime explosion which exists in the current processes, and as such, the present process is very commercially appealing.

Simultaneously with the vaporization of the aqueous oxime solution in vaporization pot 16, a water-immiscible organic solvent is vaporized by any known manner; for example, the water-immiscible organic solvent may be fed through tube 22 in the direction of arrow 24 into organic stripper or vaporization pot 26. For a continuous mode of operation, the water-immiscible organic solvent is fed as needed into vaporization pot 26; for a batch mode of operation, the total water-immiscible organic solvent is placed in vaporization pot 26 at the start of the operation.

Any water-immiscible organic solvent may be used herein. The organic solvent needs to be water-immiscible so that phase separation occurs at a later step of the process. Further, these organic solvents should possess good solubility characteristics toward the oxime used. It is necessary that the solvent be able to extract the oxime from the aqueous oxime solution vapor. The term "good solubility" as used herein means solvents wherein the oxime is soluble at about 1 g/100 ml to about 70 g/100 ml at above the solvent's boiling point. Preferably, the oxime is soluble at about 15 g/100 ml to about 30 g/100 ml. Preferably, the water-immiscible organic solvents include toluene (bp=110° C.), ethyl acetate (bp=77° C.), carbon tetrachloride (bp=77° C.), chloroform (bp=61° C.), methylene chloride (bp=41° C.), diethyl ether (bp=35° C.), benzene (bp=80° C.), and cyclohexane (bp=81° C.). These solvents are available in commercial quantities. The more preferred solvents are toluene, methylene chloride, and cyclohexane.

Further considerations in the selection of a water-immiscible organic solvent are as follows. For the phase separation which occurs at a later stage of the present process, the separation of the aqueous and organic phases occurs as long as the density of water plus oxime does not equal the density of the solvent plug oxime. So in certain situations, the density of water plus oxime may be greater than the density of the water-immiscible organic solvent plus oxime while in other cases, the density of the water-immiscible organic solvent plug oxime may be greater than the density of water plus oxime.

For the recovery of the anhydrous oxime from the removed organic phase by the vaporization of the removed organic phase and removal of liquid anhydrous oxime therefrom in a later stage of the process, the recovery of the liquid anhydrous oxime occurs as long as the boiling point of the solvent is less than the boiling point of the oxime. Advantageously, the difference between the boiling points of the oxime and the solvent is at least about 25° C. to ease removal. Thus, for example, if acetone oxime which has a boiling poitn of 135° C. is used, a useful water-immiscible organic solvent is toluene because toluene has a boiling point of 110° C.

The water-immiscible organic solvent is then vaporized in vaporization pot 26. A conventionally used vaporization pot may be used in practicing this step of the process of the present invention. The vaporization temperature of the solvent depends upon the solvent used.

The oxime-water azeotrope vapor is then fed through tube 28 in the direction of arrows 30 and 32 while the organic solvent vapor is fed through tube 34 in the direction of arrows 36 and 38. The vapors then combine together near tube 40. This feed arrangement results in a self-correcting mechanism in that if one vapor type travels toward the other vaporization pot, the other vapor type forces the first vapor type back. For example, if solvent vapor travels into tube 28, the oxime-water azeotrope vapor forces the solvent vapor back out of tube 28.

Upon mixing of the two vapors near tube 40, the solvent extracts the oxime out of the oxime-water azeotrope vapor. The collected vapors travel in the direction of arrow 42 into condenser 44. A conventionally used condenser may be used in practicing this step of the process of the present invention. The vapors condense to form a condensate which passes out of condenser 44 through tube 46 in the direction of arrow 48.

The condensate passes into phase separator 50. A conventionally used phase separator may be used in practicing this step of the present process. The condensate consists of two phases; one phase is the organic phase while the other phase is the aqueous phase. The oxime is distributed between the organic and aqueous phases.

The FIGURE illustrates the situation in the phase separator where the density of water plus oxime is greater than the density of the water-immiscible organic solvent plus oxime. Although not illustrated it should be understood that in situations where the density of the water-immiscible solvent plus oxime is greater than the density of water plus oxime, the equipment or the use thereof would be altered accordingly.

The organic phase of the condensate is removed from the aqueous phase by any manner known in the art; for example, the organic phase of the condensate may be removed from the aqueous phase in the phase separator 50 and fed through tube 52 in the direction of arrow 54 into vaporization pot 26. The majority of the oxime travels with the organic phase out of the phase separator 50. The aqueous phase is then removed from the phase separator 50 and fed through tube 56 in the direction of arrow 58 and flows into vaporization pot 16. The remainder of the oxime flows with the aqueous phase.

In vaporization pot 26, the anhydrous oxime is recovered from the removed organic phase. Upon feeding the organic phase of the two-phase condensate to vaporization pot 26, the organic phase is subjected to vaporization. Because a water-immiscible organic solvent is chosen such that the boiling point of the solvent is less than the boiling point of the oxime, the solvent vaporizes while liquid anhydrous oxime collects on the bottom of vaporization pot 26. The anhydrous oxime may be removed from the bottom of vaporization pot 26 through opening 60 in the direction of arrow 62. Because the oxime in the vaporization pot 26 was separated from the aqueous phase in the phase separator 50 and because the organic solvent is vaporized off in the vaporization pot 26, the deposited anhydrous oxime is essentially free of water and may be essentially free of organic solvent. Also as mentioned earlier, the resulting anhydrous oxime is free of higher-boiling impurities because vaporization in vaporization pot 16 eliminates such impurities from the product anhydrous oxime.

The anhydrous oxime may be removed from vaporization pot 26 through opening 60 in the direction of arrow 62 as an oxime which is as a solution in the organic solvent or which is essentially free of organic solvent. In the case of the solution, the solution may be separately treated to recover the oxime; for example, the solution may be cooled and crystallized to collect the oxime in situations where the oxime is a solid. In other instances, the solution may be separately distilled to remove the solvent and then collect the oxime as overhead product or as residue in the distillation pot. In the case of oxime which is essentially free of organic solvent, the liquid anhydrous oxime may be crystallized in a conventional manner. Anhydrous oxime is particularly useful in applications which require anhydrous conditions such as isocyanate condensation and carbamate formation, and as blocking agents for isocyanates in polyurethane coatings.

Because the organic phase in the phase separator 50 may flow into the vaporization pot 26 and because the aqueous phase in the phase separator 50 may flow into the vaporization pot 16, these phases may be reused by repeating the process steps. In other words, the organic phase flows into the vaporization pot 26 and is subjected to vaporization while the aqueous phase flows into vaporization pot 16 and is subjected to vaporization. Such phase recycling results in a more economical process.

It should be noted that although the aqueous phase flowing from the phase separator 50 to the vaporization pot 16 contains some oxime, the inorganic salt collected from the vaporization pot 16 is free of any oxime because the aqueous oxime solution from the initial feed and the recycled feed is vaporized. The transfer of the various liquid streams may be advantageously accomplished by using conventional pumps wherever appropriate.

The process of the present invention may operate in batch form wherein the vaporization pots are initially charged and the process steps are repeated until all of the oxime is anhydrous. The process may also operate in a semi-continuous manner wherein the vaporization pots are charged as needed and the liquid anhydrous oxime and inorganic salt are periodically removed from the vaporization pots. The process may also operate in a continuous mode wherein the vaporization pots are charged as needed and the liquid anhydrous oxime and inorganic salt are continuously removed from the vaporization pots.

The present invention is more fully illustrated by the following non-limiting Examples.

Examples 1 to 6 are directed to the preparation of aqueous acetone oxime solution and the production of anhydrous acetone oxime therefrom.

EXAMPLE 1

Part A - Preparation of Aqueous Acetone Oxime Solution.

A 12 liter jacketed reactor with overhead agitator, thermometer and dropping funnel, was set up and 30% hydroxylamine sulfate solution (5166 g; 18.9 eq.) was placed in the reactor. Distilled water (2160 g) was added to it and mixed. With cooling by using cold water through the jacket and agitation, 50% sodium hydroxide solution (1512 g; 18.9 eq.) was added slowly from the dropping funnel while making sure that the temperature did on exceed 40° C. At the close of addition of NaOH, the pH of the solution was 8.5. At this point, acetone (1044 g; 18.0 eq.) was added from the dropping funnel with agitation. Agitation was continued for 30 minutes. The pH had dropped to 6.5. More distilled water (5500 g) was added and a clear solution resulted. Gas chromatographic analysis showed that all acetone was consumed and that the solution contained 8.4% of acetone oxime. The total solution was drained off into a 5 gallon drum to be used as below.

Part B - Production of Anhydrous Acetone Oxime.

A 5 liter 3-necked flask was set up in a heating mantle and fitted with a 2" (5.1 cm) diameter 6' (1.8 m) column packed with ceramic saddles (aqueous stripper). A thermometer and an outlet connected to a metering pump were also attached to the flask. A second 5 liter flask as above was similarly set up (organic stripper) and the tops of the two columns were connected through a 2" vapor line to a common vertical condenser. The condenser was provided with warm (55° C.) water flowing through the jacket. The bottom of the condenser was connected to a 5 liter jacketed receiver which was also heated by warm water. The receiver was set up to act as a phase separator and thus, was provided with a drain at the bottom and an overflow point towards the top. The bottom drain was connected to a metering pump to transfer liquid to the feed point on the first column and the overflow point to another pump to transfer liquid to the feed point on the second column. The 5 gallon drum containing the acetone oxime solution was set up with a metering pump to feed the solution towards the top of the first column.

To start, 2 liters of the acetone oxime solution as prepared in Part A were placed in the aqueous stripper and heated to boiling. At the same time, toluene (2000 ml) was placed in the organic stripper and heated to boiling. Vapors from the two strippers were together condensed and a two-phase condensate collected in the phase separator. As sufficient level was built-up in the phase separator, the two pumps were started to return the aqueous and organic phases to the aqueous and organic strippers respectively.

After 30 minutes, feed of acetone oxime solution from the 5 gallon drum was started at a rate of 60 ml/minute. The operation was thus continued until the aqueous bottom temperature reached 103° C., when the pump was started to remove the salt solution free of any acetone oxime (<0.05%) from the bottom of the aqueous stripper at the rate of 55 ml per minute. At the same time, the pot temperature in the organic stripper was slowly allowed to rise to 136° C. When feeding of the acetone oxime solution was completed, the pump was stopped and at the same time, the salt-solution removal pump was stopped. The remaining operations continued for 30 minutes more with the toluene solution return slowed down. When the head temperature on the organic stripper reached 135° C. (pot temperature 139° C.), the total contents of the organic stripper bottom were quickly drained off into a pre-heated gallon bottle. The other operations were quickly shut down.

The colorless liquid quickly crystallized into colorless solid (1295 g; yield 98.6%). Gas chromatographic analysis of a solution of the crystals in acetone showed the acetone oxime was 99.6% pure with 0.4% toluene.

EXAMPLE 2

Part A - Preparation of Aqueous Acetone Oxime Solution.

Equipment as in Example 1 was used for producing cetone oxime solution. Hydroxylamine sulfate (30% solution) was neutralized with ammonia gas and treated with acetone in the usual manner and then diluted with water to form a 10.6% acetone oxime solution.

Part B - Production of Anhydrous Acetone Oxime.

Equipment as in Example 1 was used with toluene as solvent and the acetone oxime solution was fed for 4 hours after the system was equilibrated. Operation parameters are given in Table I below; AO stands for acetone oxime in Table I.

At the end, toluene was boiled off and acetone oxime was drawn off as a colorless liquid from the bottom of the organic stripper. On standing, it turned into white crystalline solid (968 g). Gas chromatographic analysis showed it to be 99.3% acetone oxime and 0.7% toluene. Karl-Fischer titration showed the water level to be less than 0.05%.

EXAMPLE 3

Part A - Preparation of Aqueous Acetone Oxime Solution.

A crude sample of colored acetone oxime crystals was used to prepare a 24% solution in water.

Part B - Production of Anhydrous Acetone Oxime.

Same equipment as in Example 1 was used, and the operation was conducted similarly with toluene as solvent over a period of 5 hours. Operation parameters are given in Table I below.

A total of 1264 g of acetone oxime was collected as colorless liquid, which turned into white crystals on standing. Yield was essentially quantitative. Purity 99.8% acetone oxime and 0.2% toluene by gas chromatography. Analysis by Karl-Fischer titration showed the water level to be less than 0.05% $H_2O$.

EXAMPLE 4

Part A - Preparation of Aqueous Acetone Oxime Solution.

The same equipment and procedure as in Example 1 were used. A crude dilute solution of hydroxylamine sulfate (11.5%) containing ammonium sulfate (18.8%) and sulfuric acid (9.8%) (referred to as Raschig solution) was used with acetone and ammonia gas as the base. Thus, a 5% solution of acetone oxime in water containing ammonium sulfate was prepared.

Part B - Production of Anhydrous Acetone Oxime.

The same equipment and procedure as in Example 1 were used. Toluene was used as the solvent and the acetone oxime solution prepared above was fed for a total of 4½ hours. Operation parameters are given in Table 1 below. At the end, toluene was evaporated off from the organic stripper and 818 g of molten acetone oxime, which crystallized on standing, was drawn off. Purity 98.9%, the major impurity being toluene. Analysis by Karl-Fischer titration showed that it contained less than 0.05% $H_2O$.

EXAMPLE 5

Part A - Preparation of Aqueous Acetone Oxime Solution.

Acetone oxime solution was produced exactly as in Example 1 using hydroxylamine sulfate solution (30%), sodium hydroxide solution, and acetone. The mixture was diluted with distilled water and a solution containing 8.6% acetone oxime with sodium sulfate was obtained.

Part B - Production of Anhydrous Acetone Oxime.

Equipment in Example 1 was modified so that continuous removal of hot acetone oxime from the bottom of the organic stripper was possible. Thus, the bottom of the organic stripper was connected through a line to a pump and in turn to a glass gallon bottle. The line was insulated and the pump was kept warm by blowing hot air using a blower.

Toluene was used as solvent and the aqueous acetone oxime solution was fed to the aqueous stripper. The organic stripper was maintained at terminal temperature conditions so that the least amount of toluene was left in the port and thus drawn off by the pump with molten acetone oxime. Operation parameters are given in Table I below.

The continuous operation was maintained for 4 hours after equilibration and 845 g liquid acetone oxime which crystallized on standing was collected. Gas chromatographic analysis of the crystals showed it to be 99.2% pure acetone oxime and 0.8% toluene. Water content was determined to be less than 0.05% by the Karl-Fischer method.

EXAMPLE 6

Part A - Preparation of Aqueous Acetone Oxime Solution.

The same equipment as in Example 1 was used and acetone oxime solution was prepared using 30% hydroxylaine sulfate solution, acetone, and sodium hydroxide solution. Thus, a solution containing 7.5% acetone oxime and 7.7% sodium sulfate was used as the feed below.

Part B - Production of Anhydrous Acetone Oxime.

Except for the following changes, the same equipment as in Example was used. The modifications were that (a) the return line from the bottom of the phase separator was connected through the pump to the organic stripper and (b) the return line from the top of the phase separator was connected through the pump to the aqueous stripper.

The equipment was operated as in Example 1, except that methylene chloride was used as solvent. The aqueous acetone oxime solution prepared above was fed into the aqueous stripper for 5½ at the end o f which the methylene chloride was stripped off and 1169 g of 99.95% pure acetone oxime was drawn off as colorless liquid, which crystallized into white crystalline solid on standing. Water level in the sample was analyzed by Karl-Fischer method and found to be less than 0.05% $H_2O$. Details of the operation parameters are given in Table II below; AO stands for Acetone Oxime in Table II.

TABLE I

| | EXAMPLES | | | |
| --- | --- | --- | --- | --- |
| | #2 | #3 | #4 | #5 |
| Aqueous stripper: | | | | |
| Feed conc. | 10.6% AO | 24% AO | 5% AO | 8.6% AO |
| Feed rate | 38.5 g/min | 17.6 g/min | 60.4 g/min | 41.5 g/min |
| Pot temp. | 102.5° C. | 101° C. | 102.5° C. | 102° C. |
| Overhead temp. | 98° C. | 98.5° C. | 98° C. | 98° C. |
| Condenser temp. | 53° C. | 54° C. | 56° C. | 53° C. |
| Phase Separator: | | | | |
| Temp. | 53° C. | 54° C. | 56° C. | 53° C. |
| Top organic phase | 29.6% AO | 32.9% AO | 28.4% AO | 31.2% AO |
| Bottom aqueous phase | 16.3% AO | 24.7% AO | 14.3% AO | 17.5% AO |
| Organic stripper: | | | | |
| Pot temp. | 120° C. | 132° C. | 131° C. | — |
| Overhead temp. | 108° C. | 107° C. | 108° C. | — |
| Terminal pot temp. | 138.5° C. | 139.5° C. | 139° C. | 138.5° C. |
| Terminal overhead temp. | 135° C. | 135.5° C. | 135° C. | 135° C. |

Examples 7 to 8 are directed to the preparation of aqueous acetaldoxime solution and the production of anhydrous acetaldoxime, i.e., acetaldehyde oxime, therefrom.

EXAMPLE 7

Part A - Preparation of Aqueous Acetaldehyde Oxime.

A 52% aqueous solution of acetaldehyde oxime commercially available was used as is for the feed. It was pure except for the presence of about 0.5% acetonitrile.

Part B - Production of Anhydrous Acetaldehyde Oxime.

The equipment as in Example 6 was used, with methylene chloride as solvent and operated similarly. The acetaldehyde oxime solution was fed for 3½ hours at the end of which methylene chloride was distilled off and the acetaldehyde oxime collected drained off from the bottom of the organic stripper. A colorless liquid (2723 g) was collected and analyzed by gas chromatography. Purity - 98.1% acetaldehyde oxime, 1.2% acetonitrile, 0.5% $CH_2Cl_2$. Karl-Fischer titration analysis showed less than 0.05% $H_2O$.

Details of the operation parameters are given in Table II below; AAO stands for Acetaldehyde Oxime in Table II.

EXAMPLE 8

Part A - Preparation of Aqueous Acetaldehyde Oxime Solution

Acetaldehyde oxime was prepared in the same equipment same as in Example 1. Crude hydroxylamine sulfate solution (Raschig) as in Example 4 was used and neutralized with ammonia gas and reacted with acetaldehyde in the usual manner. After diluting with water, a 10.5% of acetaldehyde oxime was obtained containing ammonium sulfate and small quantity of acetonitrile.

Part B - Production of Anhydrous Acetaldehyde Oxime

Equipment same as in Example 6 was used. The above solution of acetaldehyde oxime was fed for a total of 5 hours at the end of which the acetaldehyde oxime produced was drained off as in Example 7 after removing methylene chloride. yield 1269 g. Operation parameters are given in Table II below.

GC analysis of the liquid product showed it to be 95.9% acetaldehyde oxime, 3.8% acetonitrile, and 0.3% methylene chloride. Analysis by Karl-Fischer showed water content to be less than 0.05%.

TABLE II

| | EXAMPLES | | |
|---|---|---|---|
| | #6 | #7 | #8 |
| Aqueous stripper: | | | |
| Feed conc. | 7.5% AO | .52.0% AAO | 10.5% AAO |
| Feed rate | 47.9 g/min | 25 g/min | 41.5 g/min |
| Pot temp. | 102.5° C. | 101.5° C. | 103.5° C. |
| Overhead temp. | 99.5° C. | 97° C. | 99° C. |
| Condenser: Temp. | 22° C. | 21° C. | 23° C. |
| Phase Separator: | | | |
| Temp. | 22° C. | 21° C. | 23° C. |
| Top aqueous phase | 8.0% AO | 23.3% AAO | 13.6% AAO |
| Bottom organic phase | 16.3% AO | 26.6% AAO | 7.2% AAO |
| Organic stripper: | | | |
| Pot temp. | 126° C. | 55° C. | 96° C. |
| Overhead temp. | 41.5° C. | 41.5° C. | 41° C. |
| Terminal pot temp. | 137.5° C. | 115.5° C. | 116.5° C. |
| Terminal overhead temp. | 135.5° C. | 109.5° C. | 113° C. |

Having described the invention in detail and by reference to preferred embodiments thereof, it will be apparent that modifications and variations are possible without departing from the scope of the invention defined in the appended claims.

What is claimed is

1. A process for the production of anhydrous oxime comprising the steps of:

(a) vaporizing an azeotrope of oxime and water;
(b) vaporizing a water-immiscible organic solvent for the oxime wherein the boiling point of said solvent is lower than the boiling point of said oxime;
(c) combining said vapors together;
(d) condensing said collected vapors;
(e) removing the organic phase of said condensate from the aqueous phase; and
(f) recovering anhydrous oxime from said removed organic phase.

2. The process of claim 1 wherein said step (f) comprises vaporizing said removed organic phase and removing liquid anhydrous oxime.

3. The process of claim 1 wherein said water-immiscible organic solvent is methylene chloride.

4. The process of claim 1 wherein said water-immiscible organic solvent is toluene.

5. The process of claim 1 wherein the difference between said boiling points of said oxime and said solvent is at least about 25° C.

6. The process of claim 1 wherein said oxime has a boiling point of less than about 155° C.

7. The process of claim 1 wherein said oxime has a boiling point of less than about 135° C.

8. The process of claim 1 wherein said aqueous oxime solution is aqueous acetaldoxime.

9. The process of claim 1 wherein said aqueous oxime solution is aqueous acetone oxime.

10. The process of claim 9 wherein said aqueous acetone oxime solution is prepared by treatment of acetone with hydroxylamine sulfate and sodium hydroxide.

11. The process of claim 10 wherein after said step (a), said salt is removed from said aqueous oxime solution.

12. The process of claim 1 wherein the density of water plus oxime is greater than the density of said water-immiscible organic solvent plus oxime.

13. The process of claim 1 wherein the density of said water-immiscible organic solvent plus oxime is greater than the density of water plus oxime.

14. The process of claim 9 wherein said aqueous acetone oxime solution is prepared by treatment of acetone with hydroxylamine sulfate and ammonia.

15. The process of claim 9 wherein said aqueous acetone oxime solution is prepared by treatment of acetone with Raschig solution and ammonia.

16. The process of claim 1 wherein the oxime is present in said aqueous oxime solution in an amount of about 1 to about 70% by weight.

17. The process of claim 1 wherein after said step (e), said removed organic phase is used again in said step (b).

18. The process of claim 1 wherein said aqueous phase of said condensate is removed from the organic phase.

19. The process of claim 18 wherein said removed aqueous phase is used again in said step (a).

20. The process of claim 1 wherein said process operates in a continuous mode.

21. The process of claim 1 wherein said process operates in a batch mode.

* * * * *